(12) United States Patent
Jiang et al.

(10) Patent No.: US 10,392,472 B2
(45) Date of Patent: Aug. 27, 2019

(54) BIODEGRADABLE CROSS-LINKED POLYMER AND METHODS OF PREPARING THE SAME

(71) Applicant: SHANGHAI MICROPORT MEDICAL (GROUP) CO., LTD., Shanghai (CN)

(72) Inventors: Hongyan Jiang, Shanghai (CN); Qiyi Luo, Shanghai (CN); Juan Hou, Shanghai (CN); Yahong Kang, Shanghai (CN); Jing Wang, Shanghai (CN); Wei Wang, Shanghai (CN)

(73) Assignee: Shanghai Microport Medical (Group) Co., Ltd., Shanghai (CN)

( * ) Notice: Subject to any disclaimer, the term of this patent is extended or adjusted under 35 U.S.C. 154(b) by 0 days.

(21) Appl. No.: 15/922,141

(22) Filed: Mar. 15, 2018

(65) Prior Publication Data

US 2018/0265630 A1    Sep. 20, 2018

Related U.S. Application Data

(62) Division of application No. 14/434,377, filed as application No. PCT/IB2013/002496 on Oct. 9, 2013, now Pat. No. 9,951,178.

(30) Foreign Application Priority Data

Oct. 9, 2012   (CN) .......................... 2012 1 0380316
Oct. 9, 2012   (CN) .......................... 2012 1 0380863

(51) Int. Cl.
| | |
|---|---|
| *C08J 3/24* | (2006.01) |
| *C08J 3/28* | (2006.01) |
| *A61F 2/915* | (2013.01) |
| *A61L 31/06* | (2006.01) |
| *A61L 31/14* | (2006.01) |
| *C08G 63/08* | (2006.01) |
| *C08G 63/64* | (2006.01) |
| *C08G 63/91* | (2006.01) |
| *C08L 67/04* | (2006.01) |

(52) U.S. Cl.
CPC ............ *C08G 63/912* (2013.01); *A61F 2/915* (2013.01); *A61L 31/06* (2013.01); *A61L 31/148* (2013.01); *C08G 63/08* (2013.01); *C08G 63/64* (2013.01); *C08J 3/24* (2013.01); *C08J 3/28* (2013.01); *A61F 2002/91558* (2013.01); *A61F 2002/91566* (2013.01); *A61F 2002/91575* (2013.01); *A61F 2002/91583* (2013.01); *A61F 2210/0004* (2013.01); *C08J 2300/16* (2013.01); *C08J 2300/206* (2013.01); *C08J 2367/00* (2013.01)

(58) Field of Classification Search
None
See application file for complete search history.

(56) References Cited

U.S. PATENT DOCUMENTS

| | | |
|---|---|---|
| 5,059,211 A | 10/1991 | Stack et al. |
| 5,306,286 A | 4/1994 | Stack et al. |
| 6,338,739 B1 | 1/2002 | Datta et al. |
| 2001/0029398 A1 | 10/2001 | Jadhav |
| 2002/0019661 A1 | 2/2002 | Datta et al. |
| 2002/0143388 A1 | 10/2002 | Datta et al. |
| 2002/0188342 A1 | 12/2002 | Rykhus, Jr. et al. |
| 2003/0114552 A1* | 6/2003 | Schacht ............... A61L 27/16 523/113 |
| 2003/0144730 A1 | 7/2003 | Datta et al. |
| 2005/0177246 A1 | 8/2005 | Datta et al. |
| 2007/0129784 A1 | 6/2007 | Lendlein et al. |

* cited by examiner

*Primary Examiner* — Ana L. Woodward
(74) *Attorney, Agent, or Firm* — Muncy, Geissler, Olds & Lowe, P.C.

(57) ABSTRACT

A biodegradable cross-linked polymer and methods of preparing same are provided. The biodegradable cross-linked polymer is formed from a biodegradable polymeric material having two or more arms, which is a random copolymer formed of a first monomer and a second monomer different from the first monomer. The first monomer is selected from the group consisting of L-lactide, DL-lactide, glycolid, ε-caprolactone, trimethylene carbonate, p-dioxanone, amino acid-derived polycarbonates and polyorthoesters. The second monomer is one or two selected from the group consisting of D-lactide, DL-lactide, glycolide, ε-caprolactone, trimethyl carbonate, salicylic acid, carbonates, amino acids and derivatives thereof. The biodegradable polymeric material has a molecular weight of from 5,000 to 1,200,000 and an intrinsic viscosity of from 0.1 to 9.0 dl/g. Each of the terminal groups on the arms of the biodegradable polymeric material is selected from the group consisting of hydroxyl amino and carboxyl groups.

12 Claims, 3 Drawing Sheets

BIODEGRADABLE CROSS-LINKED POLYMER AND METHODS OF PREPARING THE SAME

CROSS-REFERENCE TO RELATED APPLICATION

This application is a divisional of U.S. patent application Ser. No. 14/434,377, filed Oct. 9, 2013, which claims priority of co-pending International Application No. PCT/IB2013/002496 filed Oct. 9, 2013, for which priority is claimed under 35 U.S.C. § 120; which claims priority to Chinese patent application number 201210380316.9, filed on Oct. 9, 2012 under 35 U.S.C. § 119; and Chinese patent application number 201210380863.7, filed on Oct. 9, 2012 under 35 U.S.C. § 119; the entire contents of all of which are incorporated by reference.

TECHNICAL FIELD

The present invention relates to medical appliances and, in particular, to biodegradable cross-linked polymers, vascular stents, and methods of manufacturing the same.

BACKGROUND

Since the 1970s, biodegradable polymeric materials have been extensively used in medical applications, particularly in biodegradable surgical sutures, medical adhesives, biodegradable bone fixation devices, sustained drug release, recent research in biodegradable stents, etc.

Biodegradable polymeric materials are thermoplastic or cross-linked materials. Thermoplastic biodegradable polymeric materials feature long-chain linear molecules. While such materials are soluble in compatible solvents and can be easily molded and processed using injection, extrusion and other common forming technologies, they suffer from an obvious disadvantage of exhibiting stress relaxation behavior.

Cross-linked polymers are three-dimensional networks formed by adding crosslinking agents during the polymerization of monomer or by introducing crosslinkable reactive groups in molecular chains of a linear polymer and then inducing the reaction of the reactive groups on different chains of the polymer by means of radiations, ultraviolet (UV) light, heat or the like. Cross-linked polymers swell rather than dissolving in compatible solvents. Their molding can be performed either before or after the crosslink reaction and the latter case requires the use of special equipment. Although cross-linked polymers exhibit higher structural and dimensional stability and reduced stress relaxation behavior compared to linear polymers, they are disadvantageous in requiring special equipment and technologies for their molding.

In previous research, synthesis of cross-linked polymers was mostly for producing hydrogels and investigating shape memory behavior of the materials. Because such synthesis usually involved complicated multi-step synthesis of prepolymers, its control was difficult, making it only suitable to be carried out in laboratories for research purposes. Additionally, since materials used in, and by-products produced from, such synthesis were toxic and difficult to be completely removed, use of them in the medical field has not been considered.

In References (1) and (2), the authors introduce their synthesis of cross-linked poly(butyl acrylate) networks and investigations of shape memory behavior of the materials. These cross-linked polymers are both prepared by crosslinking an optically or thermally crosslinkable polycaprolactone macromonomers obtained from methacryloyl chloride in the presence of tetrahydrofuran (or 2-dichloroethane) and an excess of triethylamine as a catalyst. During the reaction, a side reaction will occur between methacryloyl chloride and excessive triethylamine, and triethylamine hydrochlorides remaining in the product are difficult to be completely removed. The authors also propose a cross-linked shape memory polymer defined in claims 1 and 17 of patent Reference (3). The major purpose of this application is for claiming the protection of the cross-linked shape memory polymer which has at least two soft polymeric segments. In addition, exemplary cross-linked shape memory polymers presented in the application exhibit an elastic modulus of only about 71 MPa. With similarity to those of References (1) and (2), in this polymer material, only the cross-linked segments are biodegradable, while the butyl acrylate content that makes a predominant part is non-biodegradable. Further, the preparation of this cross-linked polymer is also associated with the issues of involving multiple synthesis steps, causing remains of by-products and using excessive solvents, arising from the use of the same prepolymer synthesis process as those of References (1) and (2).

Claims 1 and 12 of patent Reference (4) describe a cross-linked biodegradable polymer prepared based on a polymer made from the polycondensation of glycerol and a bifunctional diacid as monomers. This biodegradable polymer has a very low elastic modulus that is ≤5 MPa.

Patent Reference (5) discloses a cross-linked polyester elastomer. However, this polymer also has a very low elastic modulus of <1.5 MPa.

Existing stents used in the treatment of postoperative vascular restenosis and other conditions typically include metal stents, drug-eluting metal stents and biodegradable metal stents. Although the continuously progressing technology in the field of metal stents has addressed the issue of post-PTCA elastic recoil, intimal hyperplasia and other complications caused by intimal injury and the presence of metallic foreign bodies still remain unsolved. Drug-eluting metal stents can achieve an extent of intimal hyperplasia inhibition and a reduced incidence of restenosis, but due to the inevitable stimulating effect as metallic foreign bodies, their use is associated with prolonged administration of antiplatelet drugs. Further, metal stents may impede beneficial vascular remodeling after implantation.

The occurrence of restenosis is strongly time-dependent. Biodegradable stents are temporary stents which stay in vivo across specific pathological processes and disappear after fulfilling their therapeutic functions, thus avoiding exerting a long-term foreign body effect on the human body. In addition, biodegradable stents can be further used as carriers for sustained drug release and ultimately achieve intimal hyperplasia inhibition through the drug release.

For these reasons, biodegradable stents have received considerable attention. In the recent twenty years, many biodegradable stents have been made from various polymeric materials, such as L-polylactic acids (i.e., poly(L-lactide)), DL-polylactic acids (i.e., poly(L-lactide-co-D-lactide)), copolymers of L-lactide and other monomers, polycaprolactones and other thermoplastic polymeric materials, as well as their blends, or braided from fibers of these materials. In these materials, poly(L-lactide) are most studied. During the period from 1998 to 2000, human experiments related to poly(L-lactide)-based coronary stents were conducted in Japan. In 2006, Abbott commenced human experiments in Europe about a poly(L-lactide)-based drug-eluting coronary stent and acquired the CE Mark in 2011, leading to the debut of the first biodegradable cardiovascular stent product allowed to enter the market. For more information in this regard, reference can be made to non-patent References 1-14 and patent references such as, for example, U.S. Pat. Nos. 5,059,211A and 5,306,286A describing a biodegradable stent formed from a roll-up polymeric sheet, US20020143388A1, US20020019661A1, U.S. Pat. No. 6,338,739B1 and US20010029398A1 describing biodegradable stents formed from a blend of two biodegradable thermoplastic polymers, US20030144730A1 and US20050177246A1 describing a helical or tubular stent formed from absorbable fibers each having an inner core and an outer layer, and US20020188342A1 describing a braided stent formed from resorbable fibers.

However, most of commonly used polymeric materials have drawbacks as follows: insufficient mechanical strength, which makes stents made of such materials less resistant to radial compressing forces and easily to be broken by gripping pressure; stress relaxation behavior, which results in unstable performance of the stents and radial strength decreasing with time; and short shelf-lives. Compared to metallic materials, polymeric materials have much weaker mechanical properties. In contrast to elastic moduli of most metallic materials that are higher than 100 GPa, those of strongest polymeric materials are on the order of several GPa and those of aforementioned polylactic acid polymers for making biodegradable vascular stents are about 2.7 GPa. For example, US20070129784A1 describes a stent made from a shape memory polymer having cross-linked polymer. The polymer can be either a thermoplastic polymer network or a polymer blend exhibiting shape memory characteristics. However, polymer networks have very undesirable mechanical properties, for example, low elastic moduli in the range of 0.5-50 MPa, and show stress relaxation behavior, i.e., gradually decreasing stress with time at a given temperature and strain rate. In order to reduce the effect of such shortcomings, polymeric stents are typically made to have walls that are much thicker than those of metallic ones. This not only leads to non-compact dimensions of the stents but also renders them unable to provide a biodegradation rate compatible with the duration of healing of a vascular lesion where the stent is deployed.

Therefore, the conventional cross-linked polymers cannot meet the requirements for use as materials for developing medical devices in terms of mechanical properties, biocompatibility and controlled biodegradation. In addition, the complexity and excessive use of solvents in their synthesis have imposed a great challenge for controlled mass production. There is thus a need for novel cross-linked biodegradable polymers and methods of manufacturing them. Further, there is also a need for biodegradable vascular stents having sufficient mechanical strength, high elastic moduli at body temperature, compact sizes, sufficient radial strength for supporting blood vessels, minimal compression in blood vessels, stable performance, high resistance to gripping pressure, adequate shelf-lives and capability of providing a biodegradation rate compatible with the duration of healing of the vascular lesion.

SUMMARY OF THE INVENTION

In order to overcome the above described shortcomings of the prior art, the present invention provides novel cross-linked biodegradable polymers, vascular stents, and method of manufacturing them.

Specifically, the present invention provides a biodegradable cross-linked polymer which is obtained by bonding crosslinkable reactive groups to terminal groups of biodegradable prepolymer having two or more arms and then subjecting the prepolymer to thermal polymerization and/or light irridation. The cross-linked biodegradable polymer may have an elastic modulus of from 10 MPa to 4,500 MPa and a biodegradation rate of from 3 months to 36 months.

According to the present invention, the biodegradable prepolymer having two or more arms may be selected from: n-arm-poly(L-lactide), n-arm-poly(L-lactide-co-glycolide), n-arm-poly(L-lactide-co-D-lactide), n-arm-poly(L-lactide-co-DL-lactide), n-arm-poly(L-lactide-co-ε-caprolactone), n-arm-poly(L-lactide-co-trimethyl carbonate), n-arm-poly (DL-lactide), n-arm-poly(DL-lactide-co-glycolide), n-arm-poly(DL-lactide-co-ε-caprolactone), n-arm-poly(DL-lactide-co-trimethyl carbonate), n-arm-poly(ε-caprolactone), n-arm-poly(ε-caprolactone-co-glycolide) and n-arm-poly(ε-caprolactone-co-trimethyl carbonate), wherein n=2, 3 or 4, and if the biodegradable prepolymer is a copolymer, the second comonomer is present in an amount of from 1% to 80%.

According to the present invention, each of the terminal groups on the arms of the prepolymer may be selected from hydroxyl group, amino group or carboxyl group, and preferably hydroxyl group.

According to the present invention, the crosslinkable reactive groups are bonded to the terminal groups of the prepolymer through the reaction of the prepolymer and an acrylate or methacrylate containing functional groups including, but not limited to, acid anhydride, acid, acyl chloride, isocyanate and propylene oxide groups, such as, for example, methacrylic anhydride, 2-isocyanatoethyl methacrylate, epoxypropyl methacrylate, etc.

According to the present invention, the prepolymer having the two or more (n) arms may be formed by adding an initiator containing two or more (n) hydroxyl groups to a monomer.

According to the present invention, the initiator may be an initiator having two hydroxyl groups, preferably ethylene glycol, 1,4-butylene glycol, n-decanediol, tripropylene glycol, triethylene glycol, triethylene glycol dimethacrylate, triethylene glycol dimethyl ether, triethylene glycol mono-11-mercaptoundecyl ether, triethylene glycol monobutyl ether, triethylene glycol methyl ether methacrylate, polyethylene glycol (PEG) having a molecular weight of 100-10,000, poly(tetrahydrofuran) glycol (polyTHF) having a molecular weight of 100-10,000 or poly(ε-caprolactone) glycol (PCL) having a molecular weight of 100-10,000; an initiator having three hydroxyl groups, including but not limited to, polycaprolactone triol (having a molecular weight of 300 or 900), trihydroxy polyoxypropylene ether, 1,2,3-heptanetriol, 1,2,6-hexanetriol, trimethylolpropane and 3-methyl-1,3,5-pentanetriol; or an initiator having four hydroxyl groups, such as 1,2,7,8-octanetetrol, propoxylated pentaerythritol, dipentaerythritol and pentaerythritol.

The present invention also provides a method of preparing the said cross-linked polymer. The method includes:

(1) synthesis of a biodegradable polymeric prepolymer having two or more (n) arms from a cyclic monomer and an initiator in the presence of a catalyst by ring-opening polymerization;

(2) formation of a crosslinkable polymeric prepolymer by bonding crosslinkable reactive groups to terminal groups of the biodegradable polymeric prepolymer through reaction of the terminal groups with, for example, methacrylic anhydride or 2-isocyanatoethyl methacrylate; and (3) crosslinking of the prepolymer by thermal polymerization and/or light irradiation and formation of a cross-linked polymer.

According to the present invention, the prepolymer may have a molecular weight of from 2,000 to 100,000, preferably from 5,000 to 50,000.

According to the present invention, the crosslinking may be induced by thermal polymerization and/or light irradiation performed during or after a molding process.

According to the present invention, the catalyst may be stannous-2-ethylhexanote present in an amount of from 0.01% to 0.1%, with from 0.01% to 0.5% being more preferred.

The present invention discloses a method for synthesizing a biodegradable prepolymer by ring-opening polymerization. The prepolymer may have a linear or star-shaped architecture and have two or more hydroxyl, amino or carboxyl group, notably hydroxyl group, on terminals of each of its molecules. When the molecular weight of prepolymer reach a designed weight, methacrylic anhydride or 2-isocyanatoethyl methacrylate and a free radical inhibitor are added, so that the reactive group containing C=C double bond are directly bonded to the terminals of the prepolymer. After the reaction, the crosslinkable, biodegradable prepolymer obtained in a melt state may be pulverized and pelletized for further use. The whole process is simple, continuous and does not involve the use of any solvent and allows a reactor to produce several or even more than ten kilograms of the crosslinkable prepolymer. The synthesis may be performed in an even larger scale depending on the volume of the reactor. The pulverized and pelletized crosslinkable prepolymer can be formed into tubes, rods or other shapes by injection, extrusion or other molding process. In addition, crosslinking of the prepolymer may be carried out by UV light irradiation, thermal polymerization or the like during or after the molding and a biodegradable cross-linked polymer can be thereby formed.

In the molding according to the present invention, a transparent glass mold designed to form a tube may be used. The mold may include an inner core rod (column) and an outer cylinder with a larger diameter. A wall thickness of the tube to be formed is determined by diameters of the inner core rod and outer cylinder. The melt-state crosslinkable prepolymer may be injected into a space between the inner core rod and outer cylinder and then subjected to UV light or heat, such that when the inner core rod and outer cylinder are separated, a cross-linked polymer tube is obtained.

Alternatively, the molding according to the present invention may be an extrusion molding process in which the crosslinkable prepolymer may be extruded by an extruder onto a polyethylene rod, during which the rod may be simultaneously fed out from the extruder in order to ensure shape integrity of the crosslinkable tube being formed. The crosslinkable tube may receive a preliminary crosslinking treatment while it is pulling out from an outlet of the extruder and then a further crosslinking treatment after the completion of the extrusion. Afterward, with the polyethylene rod removed, a cross-linked polymer tube can also be obtained.

Cross-linked biodegradable polymers according to the present invention may have an elastic modulus of from 10 MPa to 4,500 MPa and a biodegradation rate of from 3 months to 36 months. In addition, these properties can be designed and adjusted depending on the usage of the polymer, by suitably choosing the initiator, monomer and comonomers.

The cross-linked biodegradable polymer according to the present invention differs from conventional cross-linked biodegradable polymers in terms of synthesis, composition and properties. The cross-linked biodegradable polymer according to the present invention is excellent in mechanical properties, highly compatible with tissues and blood and biodegradable at a rate that is adjustable depending on specific needs.

The present invention further provides a biodegradable vascular stent produced by laser cutting a polymeric tube, characterized in that the polymeric tube is formed from a three-dimensional cross-linked polymer network, i.e., a cross-linked polymer.

According to the present invention, the formation of the polymeric tube may include the steps of:

preparing a prepolymer, wherein the prepolymer may be a biodegradable polymer selected from the group consisting of poly(L-lactide) (L-PLA), poly(DL-lactide) (DL-PLA), poly(glycolic acid) (PGA), poly(ε-caprolactone) (PCL), poly(trimethylene carbonate) (PTMC), poly(p-dioxanone) (PPDO), amino acid-derived polycarbonates (PDTE) and polyorthoesters (POE); or a blend of any two of the above biodegradable polymers, including but not limited to, a blend of L-PLA and PCL and a blend of DL-PLA and PCL in which PCL functions to improve brittleness of the polylactides and adjust the biodegradation rate; or a copolymer of one of the above biodegradable polymers as a monomer and a second monomer present in a small amount, and wherein the prepolymer has a molecular weight of from 5,000 to 1,200,000 (first prepolymer) and an intrinsic viscosity of from 0.1 to 9.0 dl/g; and molding the prepolymer into a tube and performing a crosslinking process on the tube to obtain the said polymeric tube.

According to the present invention, the crosslinking process may include any of:

(1) bonding crosslinkable reactive groups to terminal groups of the prepolymer and inducing crosslinking of the crosslinkable reactive groups during or after the molding; and (2) in case of the terminal groups of the prepolymer being selected from the group consisting of hydroxyl, carboxyl, amino and epoxy groups, adding a crosslinking agent to induce a crosslinking reaction before or during the molding.

According to the present invention, the tube may be formed by extrusion molding or injection molding.

According to the present invention, the crosslinkable reactive groups may be bonded to the terminal groups of the prepolymer by means of an acrylate containing double bonds. The acrylate containing double bonds may be, for example, but not limited to, methacrylic acid, methacryloyl chloride, methacrylic anhydride, 2-isocyanatoethyl methacrylate, epoxypropyl methacrylate or cinnamoyl chloride.

According to the present invention, the crosslinking agent may have two or more functional groups and may be linear or star-shaped crosslinking agents containing isocyanate or epoxy group. The crosslinking agent may have a number-average molecular weight of from 500 to 100,000.

According to the present invention, the second monomer may be selected from the group consisting of D-lactide, DL-lactide, glycolide, ε-caprolactone and trimethyl carbonate. In addition, in order to impart to the stent a fine biodegradation rate compatible with the duration of healing of the vascular lesion, the amount of the second monomer may be adjusted in a range of 1-50 mol %, preferably 1-15 mol %, during the preparation of the prepolymer.

According to the present invention, the tube may have an outside diameter of from 2 mm to 10 mm and a wall thickness of from 50 μm to 250 μm.

The present invention further provides a method of manufacturing a biodegradable vascular stent. The method includes:

preparing a prepolymer, wherein the prepolymer may be a biodegradable polymer selected from the group consisting of L-PLA, DL-PLA, PGA, PCL, PTMC, PPDO, PDTE and POE; or a blend of any two of the above biodegradable polymers, including but not limited to, a blend of L-PLA and PCL and a blend of DL-PLA and PCL in which PCL functions to improve brittleness of the polylactides and adjust the biodegradation rate; or a copolymer of one of the above biodegradable polymers as a monomer and a second monomer present in a small amount, and wherein the prepolymer has a molecular weight of from 5,000 to 1,200,000 and an intrinsic viscosity of from 0.1 to 9.0 dl/g;

molding the prepolymer into a tube and performing a crosslinking process on the tube to obtain the said polymeric tube; and laser cutting the tube into the biodegradable vascular stent.

A blending or copolymerization ratio of the biodegradable polymers may be adjustable according to the requirements for strength, deformation and biodegradation rate of the stent. In case of blending or copolymerization of two polymers, the ratio may be from 1:1 to 1:20, preferably from 1:5 to 1:20.

The materials for forming the biodegradable vascular stent may be blended using methods, including but not limited to, solvent blending and melt blending. As used herein, "solvent blending" refers to a process in which two or more polymers are dissolved and mixed together in an organic solvent, while "melt blending" refers to a process in which two or more polymers are melted and mixed together at a high temperature.

The materials for forming the biodegradable vascular stent may be copolymerized using methods, including but not limited to, graft copolymerization, block copolymerization and random copolymerization. Monomers suitable for these three copolymerization methods are two or more selected from, but not limited to, L-lactic acid, D-lactic acid, hydroxyacetic acid (glycolic acid), ε-caprolactones, salicylic acid, carbonates, amino acids and their derivatives.

When preparing the prepolymer having a linear or star-shaped architecture, an initiator and a catalyst may be introduced. The initiator having two hydroxyl groups used for forming a linear prepolymer, or the initiator having three or four hydroxyl groups used for forming a star-shaped prepolymer. The initiator may be selected from, but not limited to, initiators having two hydroxyl groups, such as ethylene glycol, 1,4-butylene glycol, n-decanediol, tripropylene glycol, triethylene glycol, triethylene glycol dimethacrylate, triethylene glycol dimethyl ether, triethylene glycol mono-11-mercaptoundecyl ether, triethylene glycol monobutyl ether, triethylene glycol methyl ether methacrylate, polyethylene glycol (PEG) having a molecular weight of 100-10,000, poly(tetrahydrofuran) glycol (pTHF) having a molecular weight of 100-10,000 and poly-caprolactone glycol (PCL) having a molecular weight of 100-10,000, initiators having three hydroxyl groups, such as polycaprolactone triol (having a molecular weight of 300 or 900), trihydroxy polyoxypropylene ether, 1,2,3-heptanetriol, 1,2,6-hexanetriol, trimethylolpropane and 3-methyl-1,3,5-pentanetriol, and initiators having four hydroxyl groups, such as pentaerythritol, 1,2,7,8-octanetetrol, propoxylated pentaerythritol and dipentaerythritol. The catalyst may be selected from, but not limited to, stannous-2-ethylhexanote and dibutyltin dilaurate. The catalyst may be present in an amount of 0.01-0.1%, preferably 0.01-0.5%.

The number-average molecular weight of the prepolymer based on polylactic may be controlled in a range of from 5,000 to 100,000, preferably in a range of from 5,000 to 50,000, through adjusting a ratio of an amount of the initiator or a ratio of an amount of the second comonomer.

A biodegradation rate of the biodegradable material made of the biodegradable prepolymer is determined by a ratio of the first comonomer to the second comonomer.

The biodegradation may be tested using a shaker equipped with a water bath kept at a constant temperature of 37° C. In the test, a sample of the material with given dimensions and weight is submersed in a buffer solution having a pH of 7 in the water bath. At intervals, the sample is taken out, dried and weighed to calculate its weight loss percentages (wt %).

In case of the crosslinking agent being used, the unit or the number-average molecular weight of the prepolymer acting a first prepolymer may be the same or not as a second prepolymer used for the crosslinking agent. And the number-average molecular weight of the second prepolymer is smaller than that of the first prepolymer. The terminal groups of the first prepolymer may be, but not limited to, hydroxyl groups. The number of the arms of the first prepolymer may be determined by the number of reactive groups, for example, hydroxyl groups, of the initiator used in its synthesis, and may be usually 2, 3, or 4. The first prepolymer may have a number-average molecular weight of from 5,000 to 1,200,000 and an intrinsic viscosity of from 0.1 to 9.0 dl/g. Alternatively, the first prepolymer may also be provided as a merchandised product.

In some embodiments, the prepolymer is made from L-lactide and a second monomer. The second monomer may be one or two selected from the group consisting of D-lactide, racemic lactide, glycolide, ε-caprolactone and trimethyl carbonate. The biodegradation time of the biodegradable vascular stent made from the prepolymer is determined by the ratio of L-lactide to the second monomer, compatible with the duration of healing of a vascular lesion. The molar percentage of the second monomer may be 1-25%, preferably 1-15%. The second monomer may be one or two selected from the group consisting of D-lactides, racemic lactides, glycolides, ε-caprolactones and trimethyl carbonates.

The polymeric tube may be added with a drug during its formation such that the drug is distributed uniformly in the tube that acts as a carrier for the drug. A drug-containing biodegradable stent may be further obtained by laser cutting this polymeric tube. Alternatively, the polymeric tube may be cut into a biodegradable stent (FIG. 3) by laser firstly and the stent is then coated with the drug on its surface. Each of these two approaches enables the drug coated on the surface of or contained within the biodegradable stent to be released in a desired sustained manner to the wall of a target vessel where the stent is deployed, thus inhibiting intimal hyperplasia and reducing the incidence of restenosis.

The drug may be one or more selected from the group consisting of anticancer agents, anticoagulants, microbial immunosuppressive agents and other anti-restenosis agents.

The anticancer agents may be one or more selected from methotrexate, purines, pyrimidines, plant alkaloids, epothilones, triptolide compounds, antibiotics (notably actinomycin D), hormones and antibodies. Preferably, the anticancer agents choose from paclitaxel.

The anticoagulants may be one or more selected from heparin, aspirin, hirudin, colchicine and platelet GPIIb/IIIa receptor antagonists. The platelet GPIIb/IIIa receptor antagonists may be one or more selected from tirofiban, abciximab and eptifibatide.

The microbial immunosuppressive agents may be one or more selected from cyclosporin A, tacrolimus and its analogues, despergualin, mycophenolate esters, rapamycin and its derivatives, FR-900520 substance from Streptomyces strains, FR-900523 substance from Streptomyces strains, daclizumab, pentanamide, kanglemycin C, spergualin, prodigiosin-25C, tranilast, myriocin, cyclosporin C, bredinin, mycophenolic acid, brefeldin A and ketosteroids.

The other anti-restenosis agents may be one or more selected from batimastat, metalloproteinase inhibitors, 17β-estradiol, NO donors, 2-chlorodeoxyadenosine, 2-deoxycoformycin, fingolimod, mycophenolate sodium, $ISA_{TX}247$ (a cyclosporin A derivative), elsibucol, daclizumab, basiliximab, anti-thymocyte globulin, everolimus, methotrexate, neoral, cyclophosphamide, brequinar sodium, leflunomide and mizoribine.

Radiopacity may be imparted to the biodegradable stent either by embedding a radiopaque material such as a metallic material, for example, gold, in a terminal portion of the stent or by adding the radiopaque material to the polymeric tube during its formation. The radiopaque material may be selected from, but not limited to: biodegradable metallic materials, such as magnesium alloys; iodides, such as 6-triiodobenzoic acid, sodium 6-triiodobenzoate, iothalamic acid, metrizoic acid, iodamide, ioxaglic acid, iopamide, iohexol and iotrolan; bismuth compounds, such as bismuth oxide; barium sulfate; metal powders, such as tantalum and gold powders; other common radiopaque material; and mixtures of two or more of the above. Preferably, the radiopaque material is an iodide, a gold powder, a platinum powder, a tantalum powder, a titanium powder, a tungsten powder, or barium sulfate. The radiopaque material enables radiological imaging of the stent which helps in navigating the stent to an implantation site during the implantation and in observing whether there is a displacement of the stent after the implantation.

Biodegradable vascular stents according to the present invention are formed by laser cutting polymeric tubes which have three-dimensional cross-linked network structures and elastic moduli of from 2.5 GPa to 4.5 GPa at the room temperature and most of which have elastic moduli of up to 3 GPa even at the body temperature of 37° C. Such high mechanical strength, coupled with the three-dimensional cross-linked network structures, imparts to the stents sufficient radial compression resistance and a maximum extent of reduction in mechanical relaxation behavior, thereby reducing stent retraction. Further, the introduction of a small amount of the second monomer enables effective control of the stent biodegradation rate according to the duration of healing of the vascular lesion and makes the stents able to be biodegraded and absorbed in 1-3 years.

BRIEF DESCRIPTION OF THE DRAWINGS

Features of the invention will become apparent from the following description, taken in conjunction with the accompanying drawings. It is apparent that what are presented in the drawings are merely a few non-limiting specific embodiments of biodegradable prepolymers, cross-linked polymers and vascular stents described in this application.

FIGS. 2(a) to 2(c) show a process of making a polymeric tube having a three-dimensional cross-linked network structure in accordance with embodiments of the present invention, wherein

DETAILED DESCRIPTION

For a better understanding of the present invention, its preferred features are described in the following Examples. The description is provided merely for illustrating the features and advantages of the present invention rather than limiting its scope.

Example 1: Synthesis of Degradable Polymers Having Two or More Hydroxyl Groups (1a) the degradable polymers according to the present invention refers to, but not limited to, the following polymers, formed by melt ring-opening polymerization and having n arms/terminal groups, where n is determined by the number of arms of an initiator used in the polymerization and is ≥2, preferably 2, 3 or 4:

n-arm-poly(L-lactide), where n=2, 3 or 4,
n-arm-poly(L-lactide-co-glycolide), where n=2, 3 or 4,
n-arm-poly(L-lactide-co-D-lactide), where n=2, 3 or 4,
n-arm-poly(L-lactide-co-DL-lactide), where n=2, 3 or 4,
n-arm-poly(L-lactide-co-ε-caprolactone), where n=2, 3 or 4, and
n-arm-poly(L-lactide-co-trimethyl carbonate), where n=2, 3 or 4,
wherein each second comonomer is present in an amount of 1-80%;
n-arm-poly(DL-lactide), where n=2, 3 or 4,
n-arm-poly(DL-lactide-co-glycolide), where n=2, 3 or 4,
n-arm-poly(DL-lactide-co-ε-caprolactone), where n=2, 3 or 4, and
n-arm-poly(DL-lactide-co-trimethyl carbonate), where n=2, 3 or 4,
wherein each second comonomer is present in an amount of 1-80%;
n-arm-poly(ε-caprolactone), where n=2, 3 or 4,
n-arm-poly(ε-caprolactone-co-glycolide), where n=2, 3 or 4, and n-arm-poly(ε-caprolactone-co-trimethyl carbonate), where n=2, 3 or 4, wherein each second comonomer is present in an amount of 1-80%.

(1b) an initiator having 2, 3 or 4 hydroxyl groups was used for each of the said biodegradable polymers, and selected from, but not limited to:

initiators having two hydroxyl groups selected from:

ethylene glycol, 1,4-butylene glycol, n-decanediol, tripropylene glycol, triethylene glycol, triethylene glycol dimethacrylate, triethylene glycol dimethyl ether, triethylene glycol mono-11-mercaptoundecyl ether, triethylene glycol monobutyl ether, triethylene glycol methyl ether methacrylate, polyethylene glycol (PEG) having a molecular weight of 100-10,000, poly(tetrahydrofuran) glycol (polyTHF) having a molecular weight of 100-10,000 and poly(ε-caprolactone) glycol (PCL) having a molecular weight of 100-10,000, wherein biodegradable linear polymeric prepolymer prepared have two terminal hydroxyl groups, wherein in case of PEG; polyTHF, or PCL selected as the initiator, the biodegradable linear polymer is a PLA-PEG-PLA, PLA-polyTHF-PLA, or PLA-PCL-PLA three-block copolymer with improved hydrophilicity, biodegradation rate and mechanical properties;

initiators having three hydroxyl groups selected from:

polycaprolactone triol (having a molecular weight of 300 or 900), trihydroxy polyoxypropylene ether, 1,2,3-heptanetriol, 1,2,6-hexanetriol, trimethylolpropane and 3-methyl-1,3,5-pentanetriol, wherein a star-shaped polymer prepared have three terminal hydroxyl groups;

initiators having four hydroxyl groups selected from:

1,2,7,8-octanetetrol, propoxylated pentaerythritol, dipentaerythritol and pentaerythritol, wherein a star-shaped polymer prepared have four terminal hydroxyl groups.

(1c) the biodegradable prepolymers had a molecular weight of from 2,000 to 100,000, preferably from 5,000 to 50,000.

(1d) in the synthesis of each of the biodegradable prepolymer, stannous-2-ethylhexanote (CAS: 301-10-0) was used in an amount of from 0.01% to 0.1%, preferably from 0.01% to 0.5%.

Example 2: Functionalization of (i.e., Addition of Crosslinkable Groups to) Linear or Star-Shaped Prepolymer Containing Hydroxyl Groups

Upon the molecular weight of a biodegradable prepolymer having two or more hydroxyl groups reaching a desired value, there were added in the reactor a free radical inhibitor, for example, but not limited to, 4-methoxyphenol (with an amount of 0.01 wt %-1.0 wt %), and a calculated amount of methacrylic anhydride or 2-isocyanatoethyl methacrylate. As a result, crosslinkable active group containing unsaturated double bond were bonded to the terminal groups of the prepolymer and a crosslinkable polymeric polymer was obtained.

Example 3: Synthesis and Functionalization of 3-Arm-Star-Shaped Copolymeric Prepolymer Based on Polylactic Acid

Prior to the synthesis, a 3 L reactor was dried in vacuum at 80° C. for one hour. 2000 g L-lactide, 100 g glycolide and 14 g 1,2,6-hexanetriol were then added in the reactor under the protection of nitrogen gas and dried in vacuum at 60° C. for one hour. Thereafter, 2 g stannous-2-ethylhexanote was further added and the temperature was increased to 140° C. and maintained at 140° C. for 3 hours, forming a star-shaped copolymeric prepolymer based on polylactic acid having a number-average molecular weight of 20,000 (Equation 1).

The molecular weight of the star-shaped copolymeric prepolymer was determined by a ratio of an amount of the initiator or a ratio of an amount of the monomers and its number-average molecular weight might be controlled in a range of from 5,000 to 50,000. Upon the molecular weight of the star-shaped polylactic acid copolymeric prepolymer reaching a designed value, 48 g (0.32 mol) of methacrylic anhydride and 0.6 g (300 ppm) of 4-methoxyphenol were directly added in drops and the system was then maintained at 150° C. for 2 hours to form a crosslinkable star-shaped polymer (Equation 2). With the completion of the reaction, the reactor was cooled down to 60° C. and 5 L of ethyl acetate was added therein to dissolve the prepolymer. The solution was then slowly poured into a mixture of hexane and ethanol and a product was obtained after a precipitate in the solution was dried.

Equation 1: Formation of 3-Arm-Star-Shaped Copolymeric Prepolymer where, x=3-300 and y=1-100.

For the sake of clarity, the biodegradable prepolymer having three hydroxyl groups (n=3) in the Equation is represented hereinafter briefly as:

Equation 2: Formation of Crosslinkable 3-Arm-Star-Shaped Prepolymer Containing Crosslinkable reactive groups

Example 4: Synthesis and Functionalization of 2-Arm-Linear Prepolymer Based on Polylactic Acid Prior to the synthesis, a 3 L reactor was dried in vacuum at 60° C. for one hour. 2000 g L-lactide and 50 g Poly(THF) were then added in the reactor under the protection of nitrogen gas and dried in vacuum at 60° C. for one hour. Thereafter, 2 g stannous-2-ethylhexanote was further added and the temperature was increased to 140° C. and maintained for 3 hours, forming a linear prepolymer based on polylactic acid having a number-average molecular weight of 20,000. The molecular weight of the linear prepolymer was determined by a ratio of an amount of the initiator or a ratio of an amount of the monomer and its number-average molecular weight might be controlled in a range of from 5,000 to 50,000. Upon the molecular weight of the linear prepolymer reaching a designed value, 2-isocyanatoethyl methacrylate and 300 ppm of 4-methoxyphenol were added to form a crosslinkable linear polymer (Equation 3).

Equation 3: Formation of Crosslinkable Biodegradable Prepolymer Containing Two Crosslinkable groups where, represents the biodegradable prepolymer having 2 hydroxyl groups (n=2).

Example 5: Synthesis and Functionalization of 4-Arm-Star-Shaped Prepolymer Based on Polylactic Acid Prior to the synthesis, a 3 L reactor was dried in vacuum at 60° C. for one hour. 2000 g L-lactide, 100 g ε-caprolactone and 60 g pentaerythritol were then added in the reactor under the protection of nitrogen gas and dried in vacuum at 60° C. for one hour. Thereafter, 2 g stannous-2-ethylhexanote was further added and the temperature was increased to 140° C. and maintained for 3 hours, forming a star-shaped prepolymer having a number-average molecular weight of 18,000. The molecular weight of the star-shaped prepolymer was determined by a ratio of an amount of the initiator or a ratio of an amount of the monomers and its number-average molecular weight might be controlled in a range of from 5,000 to 50,000. Upon the molecular weight of the star-shaped copolymeric prepolymer reaching a designed value, 72 g methacrylic anhydride and 0.6 g (300 ppm) of 4-methoxyphenol were directly added and the system was then maintained to form a crosslinkable star-shaped polymer (Equation 4). With the completion of the reaction, the reactor was cooled down to 60° C. and 5 L of ethyl acetate was added therein to dissolve the prepolymer. The solution was then slowly poured into a mixture of hexane and ethanol and a product was obtained after a precipitate in the solution was dried.

Equation 4: Formation of Crosslinkable Biodegradable Prepolymer Containing Four Crosslinkable groups where, represents the biodegradable polymer having 4 hydroxyl groups (n=4).

In summary, various polymers with different molecular weights can be obtained through ring-opening polymerization of different monomers or comonomers in presence of initiators differing in terms of type, number of arms, etc. While many other biodegradable materials with different properties can be further prepared using the methods described above, their preparation is not exemplified herein.

Example 6: Crosslinking of Polymers

Each of the above-described prepared linear and star-shaped polymeric prepolymers was adequately blended with a photoinitiator such as, but not limited to, Esacure KIP 150 (with an amount of 0.1 wt %-0.5 wt %) and then melted by heat within a space between two glass blocks. In the space, PTFE film frame were arranged to adjust a thickness of the plate being formed to a desired value. Afterward, crosslinking of the melt blended was induced by UV light irradiation, thereby obtaining a standard model. The mechanical and thermal properties of the sample presented in Table 1.

In addition, biodegradation of the model was tested using a shaker equipped with a water bath kept at a constant temperature of 37° C. A sample of the formed model with given dimensions and weight was submersed in a buffer solution (pH 7) in the water bath. At intervals, the sample was taken out, dried and weighed to calculate its weight loss percentages (wt %)

TABLE 1

Mechanical and Thermal Properties of Cross-linked Biodegradable Polymers

| | Mechanical properties | | | | | Biodegradation rate: weight |
|---|---|---|---|---|---|---|
| | Room temperature (23° C.) | | Body temperature (37° C.) | | | |
| Cross-linked polymers | Elastic modulus (Gpa) | Elongation at break (%) | Elastic modulus (Gpa) | Elongation at break (%) | Thermal property (Tg/° C.) | loss percentage (wt %) at the 52$^{nd}$ week |
| PLGA (95/5) | 4.3 | 3 | 3.3 | 40 | 58 | 20% |
| PLGA (90/10) | 4.0 | 3 | 3.2 | 75 | 58 | 35% |
| PLGA (85/15) | 3.0 | 76 | 1.7 | 45 | 55 | 60% |
| PLGA (85/15)-pTHF250 | 3.6 | 18 | 3.0 | 134 | 50 | 70% |
| PLGA (85/15)-PCL500 | 3.4 | 3 | 1.8 | 140 | 44 | 60% |
| P(L-LA70-DL-LA30)-TERA | 3.1 | 125 | 0.9 | 146 | 42 | 15% |
| PLGA (85/15)-PEG400 | 2.5 | 47 | | | 40 | 75% |
| PLGA (85/15)-PEG600 | 0.7 | 150 | | | 29 | 80% |
| PLGA (85/15)-PEG1000 | 0.31 | 220 | | | 20 | 92% |
| PLGA (85/15)-PCL540 | 0.12 | 200 | | | 24 | 53% |
| PLGA (85/15)-PCL triol900 | 0.96 | 160 | | | 36 | ND |
| P(DL-LA/ε-CL90/10)-PCL540 | 2.2 | 145 | | | 35 | ND |
| PLGA (85/15)-PC500 | 3.4 | 3 | 1.8 | 140 | 44 | 55% |

In this table:
PLGA represents poly(L-lactide-co-glycolide), wherein PLGA (95/5) indicates a poly(L-lactide-co-glycolide) with a ratio of its L-lactide content to glycolide content of 95:5, and the same is applied to all the others;
PLLA represents a poly(L-lactide);
PDLLA represents a poly(DL-lactide);
P(L-LA70-DL-LA30)-TERA represents a poly(L-lactide-co-DL-lactide) having a ratio of its L-lactide content to DL-lactide content of 70:30, formed using pentaerythritol as the initiator;
pTHF250 represents a poly(tetramethylene ether) glycol with a molecular weight of 250;
PCL represents poly(ε-caprolactone) glycols, wherein PCL500 and PCL540 indicate poly(ε-caprolactone) glycols with molecular weights of 500 and 540, respectively;
PEG400, PEG600 and PEG1000 represent polyethylene glycols with molecular weights of 400, 600 and 1000, respectively;
PLGA(85/15)-PCL triol900 represents a poly(L-lactide-co-glycolide) having a ratio of its L-lactide content to glycolide content of 85:15, formed using a polycaprolactone triol with a molecular weight of 900 as the initiator;
P(DL-LA/ε-CL 90/10)-PCL540 represents a poly(DL-lactide-co-ε-caprolactone) having a ratio of its DL-lactide content to ε-caprolactone content of 90:10, formed using a polycaprolactone triol with a molecular weight of 540 as the initiator;
PLGA(85/15)-PC500 represents a poly(L-lactide-co-glycolide) having a ratio of its L-lactide content to glycolide content of 85:15, formed using a polycarbonate diol with a molecular weight of 500 as the initiator; and
ND is brief for "not determined".

It can be seen from the weight loss percentages at the 52$^{nd}$ week of the samples shown in Table 1, polymers with higher glycolide contents have increased biodegradation rates. Biodegradation rates of the polymers can be adjusted by using different initiators. For example, using a poly(tetramethylene ether) glycol as the initiator will lead to an increase in biodegradation rate because of its high hydrophilicity.

From the data in Table 1, it can also be found that, the biodegradable cross-linked polymers have elastic moduli ranging from 0.12 GPa to 4 GPa depending on their compositions, and at the body temperature, some of them maintain high elastic moduli and show improved elongations at break. That is, such polymers are tough but not brittle. Thermal properties (glass transition temperatures) of the polymers range from 20° C. to 60° C. Biodegradation rates of these polymers can be adjusted to a range of from 3 months to 36 months. Further, other parameters may also be adjusted and diversified to satisfy more practical needs.

Example 7: Formation and Crosslinking of Polymeric Tube

Each of the above-described prepared crosslinkable prepolymers was sufficiently blended with the photoinitiator Esacure KIP 150 (with an amount of 0.3 wt %) and then dried in a vacuum oven. The dried blend was extruded to form a tube or rod by a twin-screw extruder. During the extrusion, the tube or rod being formed were irradiated with UV light or other radiation to achieve rapid crosslinking.

In addition, this rapid crosslinking during the extrusion might be conducted as a preliminary polymerization process. In order to increase the stability of the tube or rod, the tube or rod was further heated at a temperature lower than a glass transition temperature of the polymer, preferably 5° C. lower than the latter, and then irradiated by UV light again until the gel content of the polymer exceeded 95%.

Crosslinking of the tube or rod might be further enhanced to a higher extent if desired.

Example 8: Polymeric Tubes with Cross-Linked Network Structure

Biodegradable vascular stents according to the present invention were formed by laser cutting respective polymeric tubes each having a three-dimensional cross-linked network structure. The formation of the polymeric tubes is described below with reference to the following sub-examples.

Example A: Prepolymer Self-Crosslinking

Figure 1A:
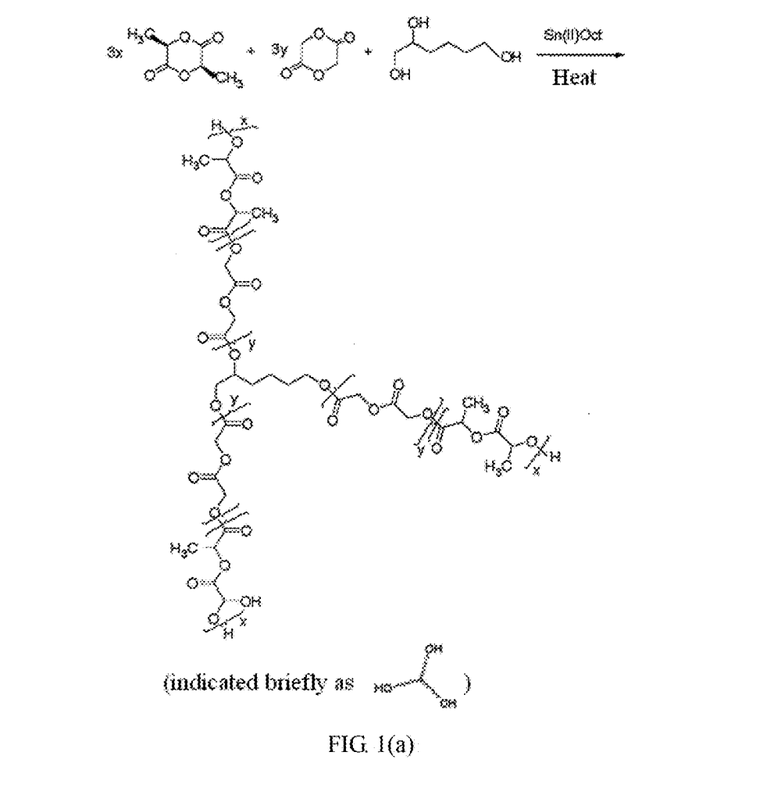
FIG. 1(a) shows synthesis of a 3-arm-star-shaped prepolymer with hydroxyl groups at its terminals, wherein x=3-300, and y=1-100.
Figure 1B:
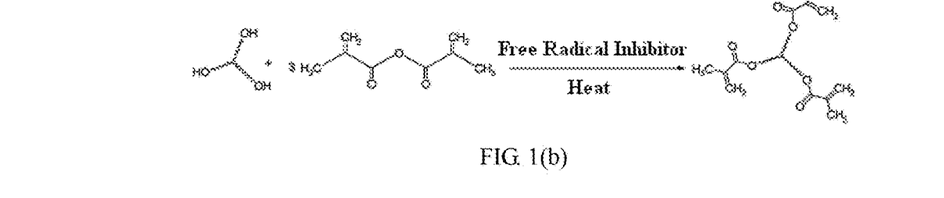
FIG. 1(b) shows formation of a crosslinkable 3-arm-star-shaped prepolymer having crosslinkable reactive groups by bonding the crosslinkable reactive groups to the terminal hydroxyl groups of the 3-arm-star-shaped prepolymer.

Synthesis of Star-Shaped Copolymeric Prepolymer Based on Polylactic Acid and Addition of Crosslinkable Groups Thereto Referring to FIG. 1(a), prior to the synthesis, a 3 L glass reactor was dried in vacuum at 80° C. for one hour, and 2100 g L-lactide, 370 g glycolide and 22 g (0.16 mol) 1,2,6-hexanetriol were then added in the reactor. After the reactor was deoxygenated by repeating the process of evacuation and argon filling, stannous-2-ethylhexanote was added therein and the reaction was run at 145° C. Upon a number-average molecular weight of the star-shaped copolymeric prepolymer reaching a designed value, 114 g (0.741 mol)

methacrylic anhydride and 0.75 g free radical inhibitor such as, for example, 4-methoxyphenol, to prepare a crosslinkable star-shaped prepolymer (FIG. 1(b)). With the completion of the reaction, the reactor was cooled down to 60° C. and 5 L of ethyl acetate was added therein to dissolve the prepolymer. The solution was then slowly poured into a mixture of hexane and ethanol and a product was obtained after a precipitate in the solution was dried.

The crosslinkable star-shaped polymer might be formed into a tube by means of extrusion, injection, or other forming technique. During or after the formation, crosslinking of the crosslinkable star-shaped polymer might be induced by UV light irradiation to form a polymeric tube with a three-dimensional cross-linked network structure. Their mechanical properties are provided in Table 2.

Figure 2A:
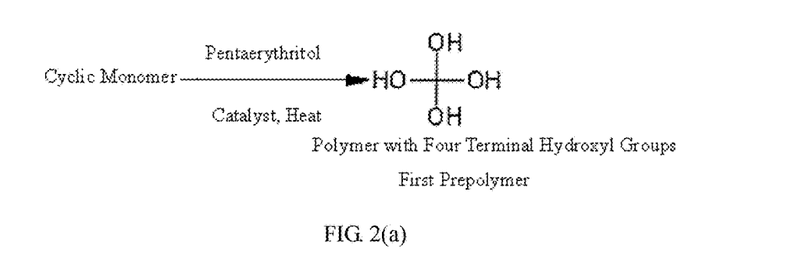
FIG. 2(a) shows synthesis of a prepolymer having terminal hydroxyl group.

Biodegradation rates of synthesized biodegradable materials were tested by a shaker at a constant temperature and indicated by their weight loss percentages, such as the data of weight loss percentages at the $52^{nd}$ week shown in Table 2, from which it can also be found that, polymers with higher glycolide contents have increased biodegradation rates. Biodegradation rates of the polymers can be adjusted by using different initiators. For example, using a poly(tetramethylene ether) glycol as the initiator will lead to an increase in biodegradation rate because of its high hydrophilicity.

mer was synthesized by ring-opening polymerization from a cyclic monomer or cyclic comonomers, such as L-lactide and ε-caprolactone (molar ratio of L-LA/ε-CL: 95/5).

Figure 2B:
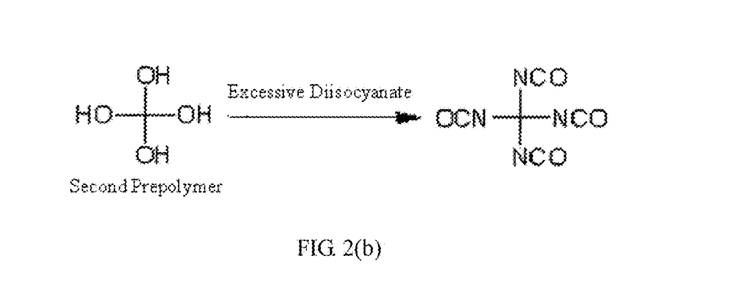
FIG. 2(b) shows synthesis of a crosslinking agent by bonding isocyanate group to terminal groups of another prepolymer.

In a second step, a crosslinking agent was synthesized, as shown in FIG. 2(b). A hydroxyl group-containing star-shaped copolymer serving as a second prepolymer was synthesized by the same approach as in the first step. For example, the second prepolymer was made from L-lactide and ε-caprolactone (molar ratio of L-LA/ε-CL: 95/5). The second prepolymer differ from the first prepolymer obtained in the first step in the number-average molecular weight controlled within a range of from 500 to 10,000. Subsequently, isocyanate groups were boned to terminals of molecules of the second prepolymer (which might be a linear or star-shaped polymer having 2, 3 or 4 arms, preferably 3 or 4 arms which might lead to a better crosslinking effect). The prepared polymer was then precipitated and rinsed until there is no residue of the isocyanate therein, thus forming the crosslinking agent.

Figure 2C:
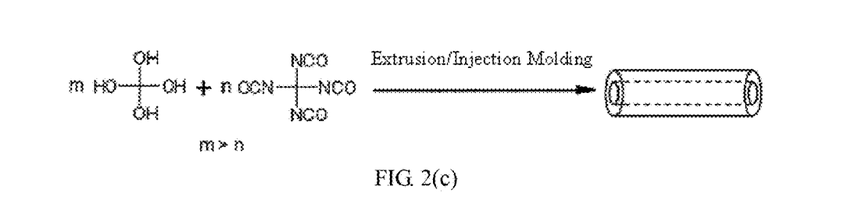
FIG. 2(c) shows formation of a tube from a blend blended adequately by the prepolymer having terminal hydroxyl group and the crosslinking agent having terminal isocyanate group.

In a third step, as shown in FIG. 2(c), the first prepolymer prepared in the first step and the crosslinking agent with terminal isocyanate groups were blended sufficiently and optionally added with a suitable amount (0.1 mol %) of a catalyst such as dibutyltin dilaurate (CAS: 77-58-7). The

TABLE 2

Mechanical Properties of Cross-linked Polymers

| Cross-linked polymers | Mechanical properties | | | | | Biodegradation Rate (in vitro biodegradation): weight loss percentage (%) at the $52^{th}$ week |
|---|---|---|---|---|---|---|
| | Room temperature (23° C.) | | Body temperature (37° C.) | | | |
| | Elastic modulus (Gpa) | Elongation at break (%) | Elastic modulus (Gpa) | Elongation at break (%) | Thermal property (Tg/° C.) | |
| PLGA (95/5) | 4.3 | 3 | 3.3 | 40 | 58 | 20% |
| PLGA (90/10) | 4.0 | 3 | 3.2 | 75 | 58 | 35% |
| PLGA (85/15) | 3.0 | 76 | 1.7 | 45 | 55 | 60% |
| PLGA (85/15)-pTHF250 | 3.6 | 18 | 3.0 | 134 | 50 | 70% |
| PLGA (85/15)-PCL500 | 3.4 | 3 | 1.8 | 140 | 44 | 60% |
| P(L-LA70-DL-LA30)-PCL540 | 3.1 | 125 | 0.9 | 146 | 42 | 15% |

In this table:
PLGA represents a poly(L-lactide-co-glycolide), wherein PLGA (95/5) indicates a poly(L-lactide-co-glycolide) with a ratio of its L-lactide content to glycolide content of 95:5, and PLGA (90/10) indicates a poly(L-lactide-co-glycolide) with a ratio of its L-lactide content to glycolide content of 90:10;
PLLA represents a poly(L-lactide);
PDLLA represents a poly(DL-lactide);
P(L-LA70-DL-LA30) represents a poly(L-lactide-co-DL-lactide) having a ratio of its L-lactide content to DL-lactide content of 70:30;
pTHF250 represents a poly(tetramethylene ether) glycol with a molecular weight of 250; and
PCL represents poly(ε-caprolactone) glycols, wherein PCL500 and PCL540 indicate poly(ε-caprolactone) glycols with molecular weights of 500 and 540, respectively.

From data in the above table, it can be seen that the cross-linked polymers synthesized in accordance with this sub-example possess high elastic moduli (>3 GPa) at the room temperature. Particularly some of them maintain high elastic moduli (>3 GPa) and exhibit high elasticity (evidenced by their elongation of ≥40% at break) at 37° C. It provides stents made of them with sufficient radial strength and resistance to compression. In addition, selecting suitable comonomers can enable the adjustment of the polymer's biodegradation rate according to the duration of healing of the vascular lesion.

Example B: Crosslinking Between Prepolymer and Crosslinking Agent

Referring to FIG. 2(a), in a first step, a biodegradable star-shaped polymeric copolymer serving as a first prepolyblend was then formed into a tube by extrusion molding or injection molding. The formed tube may be subjected to a suitable thermal treatment to obtain an enhanced crosslinking degree, thus forming a polymeric tube with the three-dimensional cross-linked network structure.

Example 9: Stents

Figure 3:
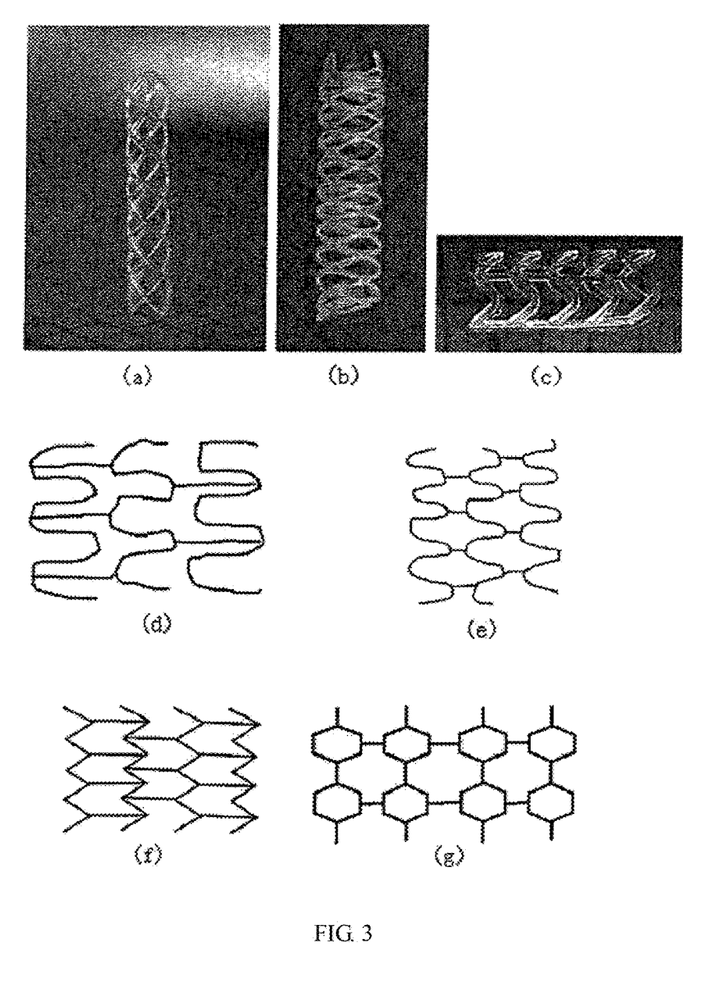
FIG. 3 shows examples of biodegradable vascular stents having different structures according to embodiments of the present invention.

In general terms, the polymeric tubes with three-dimensional cross-linked network structures might each have an outside diameter of 2-10 mm and a wall thickness of 50-250 μm. The polymeric tubes with three-dimensional cross-linked network structures obtained in accordance with the sub-examples of Example 8 might be laser cut according to practical application requirements to form biodegradable vascular stents as shown in FIG. 3.

Stent Strength and Stability

The stent shown in FIG. 3(b) having an outside diameter of 3 mm, a wall thickness of 150 μm and a length of 2 cm was submersed in a 37° C. water bath held between two plates. A tensile test machine was used to compress the stent at a rate of 10 mm/min. When the compressive deformation of the stent reaches 15%, the stress value was recorded. For each type of the stents, 10 samples were tested and the data were averaged and shown in Table 3. Another group of samples was stored in vacuum packaging bags at the room temperature for 3 months and their strength was tested in the same way. The results showed that, the stents with three-dimensional cross-linked network structures had similar radial strength to metallic stents and the radial strength was stable with time and did not show significant decrease.

TABLE 3

| Radial strength (N/mm$^2$) | Cross-linked PLA stent |
|---|---|
| On the start day | 0.131 ± 0.013 |
| 3 Months later | 0.128 ± 0.008 |

During use of a biodegradable stent according to the present invention, it needs to be compressed over a non-inflated balloon of a stent delivery system in advance. After the stent has been delivered to a lesion site of a vessel, the balloon is inflated and the stent is expanded to form a support to the lesion site. Subsequently, the balloon is deflated and withdrawn from the body together with the delivery system. The polymeric tubes prepared in accordance with Example 8 with a three-dimensional cross-linked network structure have high mechanical strength, which provide the stents with sufficient radial compression resistance. In addition, when exposed to the body temperature, the polymeric stents according to the present invention can sense temperature increase and the three-dimensional network structures can exhibit a shape memory effect. This allows the stents to gradually regain their original diameters and reduces mechanical relaxation behavior of their polymeric materials to a maximum extent, which leads to reduced occurrence of stent retraction.

Description of the foregoing examples is presented merely for facilitating the understanding of the core principles of the present invention. It is noted that while many modifications and variations can be made by those of ordinary skill in the art without departing from the inventive concept disclosed herein, it is intended that the appended claims cover all such modifications and variations.

REFERENCES (1) Kelch S, Steuer S. et al., Shape-Memory Polymer Networks from oligo[(ε-hydroxycaproate)-co-glycolate] dimethacrylates and Butyl Acrylate with Adjustable Hydrolytic Degradation Rate, *Biomacromolecules* 2007, 8, 1018-1027.
(2) Lendlein et al. Shape-Memory Polymer networks from oligo(ε-caprolactone) dimethacrylate J. Polym. Sci. Part A. 2005, 43, 1369.
(3) Langer R. et al. U.S. Pat. No. 6,388,043 B1 shape-memory polymers, 2002.
(4) Wang Y. D. et al. US2003/0118692 A1, Biodegradable polymers.
(5) Bettinger C. J. et al. WO2007/082305 A2 Biodegradable elastomers.
(6) Susawa T et al, Biodegradable intracoronary stents in adult dogs, J. Am. Coll. Cardiol. 1993, 21(supp 1), 483A.
(7) Stack R. S. et al. Interventional cardiac catheterization at Duke Medical Center. Am. J. Cardiol. 1988, 62, 3F-24F.
(8) Zidar J. P. et al, Short-term and long-term vascular tissue response to the Duke biodegradable stent. J. Am. Coll. Cardiol. 1993, 21, 439A.
(9) Tamai et al. Initial and 6-month results of biodegradable P-l-lactic acid coronary stents in humans. Circulation, 2000, 102, 399-404.
(10) Tsuji T, Tamai H, Igaki K, et al. One year follow-up biodegradable self-expanding stent implantation in humans. J Am Coll Cardiol 2001; 37(Abstr): A47.
(11) Eberhart R. C. et al. Expandable biodegradable endovascular stent. I. Fabrication and properties. Annals of biomedical engineering, 2003, 31, 667-677.
(12) Eberhart R. C. et al. Mechanical properties and in vitro degradation of bioresorbable fibers and expandable fiber-based stents, 2005, J. Biomed. Mater. Res. Part B: Appl. Biomater. 2005, 74B: 792-799.
(13) Hietala E. M. et al, Biodegradation of the copolymeric polylactide stent, J. Vascular Research, 2001, 38, 361-369.
(14) Välimaa T et al, Viscoelastic memory and self-expansion of self-reinforced bioabsorbable stents, Biomaterials, 2002, 23, 3575-3582.
(15) Ye Y. W. et al, Bioresorbable microporous stents deliver recombinant adenovirus gene transfer vectors to the arterial wall, Annals of Biomedical Engineering, 1998, 3, 398-408.
(16) Blindt R. et al, Long-term assessment of a novel biodegradable paclitaxel-eluting coronary polylactide stent, European Heart Journal, 2004, 25, 1330-1340.
(17) Venkatraman S. S. et al, Biodegradable stent with elastic memory, Biomaterials, 2006, 27(8): 1573-8.
(18) Gao R et al, A novel polymeric local heparin delivery stent: initial experimental study. J. Am. Coll. Cardiol. 1996, 27, 85A.
(19) John A. Ormiston et al. First-in-Human Implantation of a Fully Bioabsorbable Drug-Eluting Stent: The BVS Poly-L-Lactic Acid Everolimus-Eluting Coronary Stent, Catheterization and Cardiovascular Interventions 69:128-131(2007).

What is claimed is:

1. A biodegradable cross-linked polymer for manufacturing a vascular stent, wherein the biodegradable cross-linked polymer is formed from a biodegradable polymeric material having two or more arms, wherein the biodegradable polymeric material having two or more arms is a random copolymer formed of a first monomer and a second monomer different from the first monomer, wherein the first monomer is selected from the group consisting of L-lactide, DL-lactide, glycolide, ε-caprolactone, trimethylene carbonate, p-dioxanone, and the second monomer is one or two selected from the group consisting of D-lactide, DL-lactide, glycolide, ε-caprolactone, trimethyl carbonate, salicylic acid, carbonates, amino acids and derivatives thereof, and wherein the biodegradable polymeric material having two or more arms has a number-average molecular weight of from 20,000 to 1,200,000, an intrinsic viscosity of from 0.1 to 9.0 dl/g and an elastic modulus of from 2.5 GPa to 4.5 Gpa at room temperature, and wherein each of terminal groups on the arms of the biodegradable polymeric material having two or more arms is selected from the group consisting of hydroxyl, amino and carboxyl groups.

2. The biodegradable cross-linked polymer of claim 1, wherein the biodegradable cross-linked polymer is obtained by bonding crosslinkable reactive groups to the terminal groups on the arms of the biodegradable polymeric material having two or more arms, and further crosslinking the bonded crosslinkable reactive groups.

3. The biodegradable cross-linked polymer of claim 2, wherein the crosslinkable reactive groups bonded to the terminal groups of the biodegradable polymeric material having two or more arms are selected from the group consisting of (meth)acrylate and any derivative thereof.

4. The biodegradable cross-linked polymer of claim 3, wherein the crosslinkable reactive groups bonded to the terminal groups of the biodegradable polymeric material having two or more arms are selected from the group consisting of methacrylic acid, methacryloyl chloride, methacrylic anhydride, 2-isocyanatoethyl methacrylate and epoxypropyl methacrylate.

5. The biodegradable cross-linked polymer of claim 2, wherein the crosslinking is under a thermal or light irradiation condition.

6. The biodegradable cross-linked polymer of claim 1, wherein the biodegradable cross-linked polymer is obtained by mixing a crosslinking agent and the biodegradable polymeric material having two or more arms.

7. The biodegradable cross-linked polymer of claim 6, wherein the crosslinking agent is selected from linear or star-shaped crosslinking agents containing isocyanate or epoxy group, and the crosslinking agent has a number-average molecular weight of from 500 to 100,000.

8. The biodegradable cross-linked polymer of claim 6, wherein the crosslinking agent is any one, of or a blend of any two or three of n-arm-poly(L-lactide), n-arm-poly(DL-lactide), n-arm-poly(glycolic acid), n-arm-poly(ε-caprolactone), n-arm-poly(trimethylene carbonate), n-arm-poly(p-dioxanone), n-arm-poly(amino acid-derived polycarbonates) and n-arm-polyorthoesters, where n=2, 3 or 4; or the crosslinking agent is a copolymer formed of a third monomer and a fourth monomer different from the third monomer, wherein the third monomer is selected from the group consisting of L-lactide, DL-lactide, glycolide, ε-caprolactone, trimethylene carbonate, and p-dioxanone, and the fourth monomer is one or two selected from the group consisting of D-lactide, DL-lactide, glycolide, ε-caprolactone, trimethyl carbonate, salicylic acid, carbonates, amino acids and derivatives thereof.

9. The biodegradable cross-linked polymer of claim 1, wherein the second monomer accounts for 1 mol % to 50 mol % of a total amount of the first and second monomers.

10. The biodegradable cross-linked polymer of claim 1, wherein the biodegradable polymeric material having two or more arms is selected from the group consisting of n-arm-poly(L-lactide-co-glycolide), n-arm-poly(L-lactide-co-D-lactide), n-arm-poly(L-lactide-co-DL-lactide), n-arm-poly(L-lactide-co-ε-caprolactone), n-arm-poly(L-lactide-co-trimethyl carbonate), n-arm-poly(DL-lactide-co-glycolide), n-arm-poly(DL-lactide-co-ε-caprolactone), n-arm-poly(DL-lactide-co-trimethyl carbonate), n-arm-poly(ε-caprolactone-co-glycolide) and n-arm-poly(ε-caprolactone-co-trimethyl carbonate), where n=2, 3 or 4.

11. A method of preparing a biodegradable cross-linked polymer as defined in claim 1, comprising:
preparing the biodegradable polymeric material having two or more arms;
bonding crosslinkable reactive groups to the terminal groups of the biodegradable polymeric material having two or more arms; and
crosslinking the bonded crosslinkable reactive groups.

12. A method of preparing a biodegradable cross-linked polymer as defined in claim 1, comprising:
preparing the biodegradable polymeric material having two or more arms; and
mixing a crosslinking agent and the biodegradable polymeric material having two or more arms so that the crosslinking agent crosslinks with the biodegradable polymeric material.

* * * * *